US006518451B2

(12) United States Patent  
Bonda et al.

(10) Patent No.: US 6,518,451 B2  
(45) Date of Patent: Feb. 11, 2003

(54) DIESTERS OF NAPHTHALENE DICARBOXYLIC ACID

(75) Inventors: Craig A. Bonda, Wheaton, IL (US); Peter J. Marinelli, Bartlett, IL (US); Robert J. Mc Millin, Oak Lawn, IL (US)

(73) Assignee: Haarmann & Reimer, Teterboro, NJ (US)

( * ) Notice: Subject to any disclaimer, the term of this patent is extended or adjusted under 35 U.S.C. 154(b) by 82 days.

(21) Appl. No.: 09/843,262

(22) Filed: Apr. 26, 2001

(65) Prior Publication Data

US 2002/0192176 A1 Dec. 19, 2002

(51) Int. Cl.⁷ .............................................. C07C 69/76

(52) U.S. Cl. ........................... 560/80; 560/85; 514/533

(58) Field of Search ................... 560/80, 85; 424/70.6

(56) References Cited

U.S. PATENT DOCUMENTS

| | | |
|---|---|---|
| 2,607,658 A | 8/1952 | Govett et al. |
| 2,645,616 A | 7/1953 | Govett et al. |
| 2,876,163 A | 3/1959 | Garizio et al. |
| 3,255,082 A | 6/1966 | Barton |
| 3,740,421 A | 6/1973 | Schmolka |
| 4,268,499 A | 5/1981 | Keil |
| 4,278,655 A | 7/1981 | Elmi |
| 4,308,328 A | 12/1981 | Salyer et al. |
| 4,350,605 A | 9/1982 | Hughett |
| 4,383,988 A | 5/1983 | Teng et al. |
| 4,387,089 A | 6/1983 | DePolo |
| 4,489,057 A | 12/1984 | Welters et al. |
| 4,562,067 A | 12/1985 | Hopp et al. |
| 4,725,430 A | 2/1988 | Schamper et al. |
| 4,822,602 A | 4/1989 | Sabatelli |
| 4,990,690 A | 2/1991 | Onda et al. |
| 5,385,729 A | 1/1995 | Prencipe et al. |
| 5,635,166 A | 6/1997 | Galleguillos et al. |
| 5,670,140 A | 9/1997 | Deflandre et al. |
| 5,783,173 A | 7/1998 | Bonda et al. |
| 5,788,954 A | 8/1998 | Bonda et al. |
| 5,849,273 A | 12/1998 | Bonda et al. |
| 5,882,634 A | 3/1999 | Allard et al. |
| 5,976,513 A | 11/1999 | Robinson |
| 5,993,789 A | 11/1999 | Bonda et al. |
| 6,113,931 A | 9/2000 | Bonda et al. |
| 6,126,925 A | 10/2000 | Bonda et al. |
| 6,129,909 A | 10/2000 | Bonda et al. |

FOREIGN PATENT DOCUMENTS

| | | |
|---|---|---|
| FR | 1429967 | 9/1966 |
| GB | 1277557 | 6/1972 |
| JP | 04221330 | 8/1992 |
| JP | 05310530 | 11/1993 |
| JP | 07076511 | 3/1995 |
| WO | WO 99/24256 | 5/1999 |
| WO | WO 00/57850 | 5/2000 |

OTHER PUBLICATIONS

"Photostable Cosmetic Light Screening Composition", Author: Anon. Organization, UK Publication Source, Research Disclosure (Feb. 1999), 418, P175 (No. 41803). Identifier–Coden RSDSBB ISSN 0374–4363 Publisher Kenneth Mason Publications Ltd. Patent Information.

"Polyester And Copolyester Sheeting, Film And Structural Products Stabilized Against Degradation By Sunlight Or Other UV Light Sources", Author: Anon. Organization, Research Disclosure (Nov. 1994), P601 (No. 36708).

Fox, Charles, Fox Associates, Fair Lawn, New Jersey, "Gels and Sticks Review and Update", *Cosmetics & Toiletries*, vol. 99, Nov. 1984 (pp. 19, 20, 22, 24, 25, 28–30, 32, 34, 36, 38, 40, 42, 44, 47, 48, 50, 52, 54).

Fox, Charles, Charles Fox Associates Inc., Fair Lawn New Jersey, "Antiperspirants & Deodorants Review and Update" *Cosmetrics & Toiletries*, vol. 100, Dec. 1985 (pp. 27–33, 35–36, 40–41).

"Deodorant & Antiperspirant Formulary", *Cosmetics & Toiletries*, vol. 100, Dec. 1985 (pp. 65–75).

(List continued on next page.)

*Primary Examiner*—Paul J. Killos  
(74) *Attorney, Agent, or Firm*—Joseph C. Gil; Jennifer R. Seng

(57) ABSTRACT

A composition containing a diester of a naphthalene dicarboxylic acid having compound formula (I) for photochemically stabilizing dibenzoylmethane derivatives, absorbing UV radiation, imparting gloss and for stabilizing natural hair color and hair dyes against fading, and which can be used to increase the emolliency and sunscreen protection factor (SPF) of cosmetic formulations and for filtering out ultraviolet radiation from human skin:

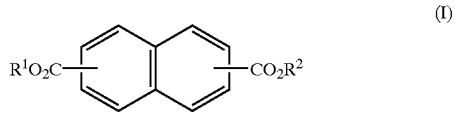

(I)

wherein $R^1$ is has the formula (II)

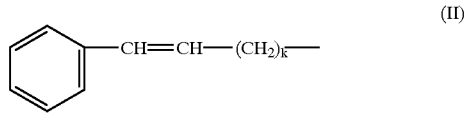

(II)

wherein k is 1 to 13, preferably 1 to 6, most preferably 1, and $R^2$, same or different, is selected from the group consisting of a compound of formula (II) wherein k is 1 to 13, preferably 1 to 6, most preferably 1, and an alkyl group, straight chain or branched, having 1 to 22 carbon atoms, and mixtures thereof. These diesters of formula (I) are quite effective in stabilizing the dibenzoylmethane derivative UV-A filter compounds making them more effective, and effective for longer periods of time.

55 Claims, 1 Drawing Sheet

OTHER PUBLICATIONS

Goldemberg, et al., "Silicones In Clear Formulations", D&CI, Feb. 1986, (pp. 34, 38, 40, 44).

STN, File Supplier, Karlsruhe, DE, File Chemical Abstracts, vol. 130, AN=158258 see the abstract XP002126186 & Research Disclosure, No. 418003, Feb. 10, 1999 p. 172 UK the whole document.

Database WPI, Section Ch, Week 200114, Derwent Publications Ltd., London, GB; AN 2001–135326 XP002166356 Anonymous: "Cosmetic emulsions containing amino acids to prevent photochemical reactions are stabilized by addition of oils such as fatty acid esters or silicones" abstract & Research Disclosure, vol. 437, No. 019, Sep. 10, 2000 Emsworth, GB.

Zouboulis, Christos C., (Department of Dermatology, University Medical Center Benjamin Franklin, The Free University of Berlin, Berlin, Germany) "Retinoids: Is there a New Approach?", IFSCC Magazine—vol. 3, No. 3 / 2000, pp. 9–19.

Zatz, Joel L., "Skin Delivery of Retinoids—Reducing The Skin Irritancy of Topical Retinoids", © 1998, 1999 Joel L. Zatz (pp. 1–8) (http://www–rci.rutgers.edu/~zatz/SkinPermeation?Retinoids.html.

Weber, Fritz et al. —"Vitamin A and Retinoids", (pp. 1–3) http://www.chem.qmw.ac.uk/iubmb/newsletter/1996/news2.html.

Maddin, S. MD, et al.—"Isotretinoin improves the appearance of photodamaged skin; Results of a 36–week, multi-center, double–blind, placebo–controlled trial" *Journal Of The American Academy Of Dermatology*, Jan. 2000, Part 1 • vol. 42• No. 1 (pp. 1–13) http://www.eblue.org/scripts/om.dll/serve. . . .

SIGMA© ProductInformation (all trans–Retinoic Acid Sigma Prod. No. R2625 Oct. 8, 1996—ARO pp. 1–3.

Kang, Sewon, M.D., et al., "Photoaging therapy with topical tretinoin: an evidence–based analysis", *Journal Of The American Academy Of Dermatology*, Aug. 1998, Part 3 •vol. 39 •No. 2 (pp. 1–9) http://www.eblue.org/scripts/om.dll/serve. . . .

Kligman, Albert M., MD, PhD., "Topical treatments for photoaged skin—separating the reality from the hype", *Postgraduate Medicin: Skin Disorders Symposium: Topical treatments for photoaged skin*, vol. 102 / No,. 2 / Aug. 1997 / Postgraduate Medicine p. 1–8 http://www.postgradmed.com/issues/1997/08_97/Kligman.htm.

Kligman, Albert M., MD, PhD., "The growing importance of topical retinoids in clinical dermatology: a retrospective and prospective analysis" *Journal Of The American Academy Of Dermatology*, Aug. 1998, Part 3•vol. 39•No. 2 (pp. 1–7) http://www.eblue.org/scripts/om.dll/serve . . . .

Hamilton, Joan O'C., "Lilly gets a Vitamin $hot from Ligand—The Retinoid Renaissance", Signals Article: The Retinoid Renaissance, published Dec. 3, 1997 (pp. 1–9) http://www.signalsmag.com/signalsmag.nsf/0/665D05084647BA28825656A006B0F9D.

Moss, G.P. (World Wide Web versions prepared by)—Department of Chemistry, Queen Mary and Westfield College, United Kingdom, "Nomenclature of Retinoids—Recommendations 1981)", International Union Of Pure And Applied Chemistry And International Union Of Biochemisty And Molecular Biology, IUPAC–IUB Joint Commission On Biochemcial Nomenclature (JCBN) pp. 1–10 http://www.chem.qmw.ac.uk/iupac/misc/ret.html.

"Retinoids", *Molecular Medicine—News from Research Laboratories* (Dec., 1997)—pp. 1–2 http://www.aston.it/biomedicine/biom0054.htm.

Chemical Abstracts Jan–Jun. 1963 Subject index, "Naphthalic Acid".

DIESTERS OF NAPHTHALENE DICARBOXYLIC ACID

FIELD OF THE INVENTION

The invention is directed to diesters of naphthalene dicarboxylic acid. More particularly, the invention is directed to the use of diesters of naphthalene dicarboxylic acid that are surprisingly effective in photochemically stabilizing dibenzoylmethane derivatives, absorbing UV radiation, and which can be used to increase the emolliency and sunscreen protection factor (SPF) of cosmetic formulations. The diesters of naphthalene dicarboxylic acid are also useful for imparting gloss and for stabilizing natural hair color and hair dyes against fading, and to impart gloss to hair.

BACKGROUND OF THE INVENTION AND PRIOR ART

It is well known that ultraviolet light having a wavelength between about 280 nm or 290 nm and 320 nm (UV-B) is harmful to human skin, causing burns that are detrimental to the development of a good sun tan. UV-A radiation, while producing tanning of the skin, also can cause damage, particularly to very lightly colored, sensitive skin, leading to reduction of skin elasticity and wrinkles.

Therefore, a sunscreen composition should include both UV-A and UV-B filters to prevent most of the sunlight within the full range of about 280 nm to about 400 nm from damaging human skin.

The UV-B filters that are most widely used commercially in sunscreen compositions are paramethoxycinnamic acid esters, such as 2-ethylhexyl paramethoxycinnamate, commonly referred to as octyl methoxycinnamate or PARSOL® MCX, having an ethyl radical extending from the 2 position of the hexyl long chain backbone; oxybenzone; and octyl salicylate.

The UV-A filters most commonly used in commercial sunscreen compositions are the dibenzoylmethane derivatives, particularly 4-(1,1-dimethylethyl)-4'-methoxydibenzoylmethane (PARSOL® 1789), and 4-isopropyl dibenzoylmethane (EUSOLEX 8020). Other dibenzoylmethane derivatives described as UV-A filters are disclosed in U.S. Pat. Nos. 4,489,057; 4,387,089 and 4,562,067 and 5,670,140, hereby incorporated by reference. It is also well known that the above described and most commonly used UV-A filters, particularly the dibenzoylmethane derivatives, such as PARSOL® 1789, suffer in photochemical stability (also called photostability) when used alone or in combination with the above-described most commercially used UV-B filters. Accordingly, when used alone or when combined with a UV-B filter, such as 2-ethylhexyl paramethoxycinnamate (PARSOL® MCX), oxybenzone and/or octyl salicylate, the PARSOL® 1789 becomes less photochemically stable, necessitating repeated, frequent coatings over the skin for sufficient UV radiation protection.

In accordance with one embodiment of the invention, it has been found, quite surprisingly, that by including one or more diesters of naphthalene dicarboxylic acid of formula (I) into a cosmetic sunscreen formulation containing a UV-A dibenzyolmethane derivative, particularly PARSOL® 1789, and/or 4-isopropyl dibenzoylmethane (EUSOLEX 8020), the dibenzyolmethane derivative is photochemically stabilized so that the dibenzyolmethane derivative-containing sunscreen composition, with or without additional sunscreen agents, such as oxybenzone and/or octyl methoxycinnamate (ESCALOL 567), is more effective for filtering out UV-A radiation; the composition filters more UV-A radiation for longer periods of time; and, therefore, the sunscreen formulation need not be applied to the skin as frequently while maintaining effective skin protection against UV-A radiation.

In accordance with another important advantage of the invention, the diesters of naphthalene dicarboxylic acids can also absorb UV light in the most damaging range of about 280 nm to 300 nm, especially over the 280 nm to 295 nm wavelength absorbance range.

By the addition of UV-B filter compounds, such as octyl methoxycinnamate, octyl salicylate, and/or oxybenzone, the compositions of the invention can maintain surprisingly effective hair color protection and can protect against UV radiation both in the UV-A and UV-B range, with or without common sunscreen additives, such as octocrylene, and/or titanium dioxide. The composition reaches a surprisingly high SPF without solid additives, such as titanium dioxide, thereby providing an exceptionally elegant feel that can be applied easily in a continuous coating for complete coverage and sunscreen protection. In the preferred compositions, the ratio of UV-A to UV-B filter compounds is in the range of about 0.1:1 to about 10:1, preferably about 0.1:1 to about 3:1, more preferably about 0.1:1 to about 0.5:1, most preferably about 0.3:1 to about 0.5:1. The preferred compositions of the invention achieve unexpectedly high SPF, e.g., higher than SPF 12, or higher than SPF 20, with the addition of surprisingly low amounts of other UV-B and UV-A filters to the PARSOL 1789, and without solid blocking compounds, such as $TiO_2$.

In accordance with another embodiment of the invention, the diesters of naphthalene dicarboxylic acid of the invention impart gloss to hair, and/or stabilize hair color against fading, particularly for hair containing a synthetic dye.

In addition, clear or transparent cosmetic formulations are particularly desirable because the consumer likens transparency to purity, and because transparent formulations have esthetic and functional appeal. Clear cosmetic formulations sometimes have been difficult to maintain stable and clear, but have been developed in each of the following areas: clear roll-ons and gels for antiperspirants; clear gel curl activators (hair moisturizers with relatively high levels of polyols); clear cosmetic sticks, including deodorant sticks and antiperspirant sticks; clear solutions; clear suntan oils; clear transdermal drug administration solutions, e.g., clear benzocaine solutions; clear aftershave compositions; transparent gel toothpastes; and clear lipsticks.

In accordance with another aspect of the invention, one or more diesters of naphthalene dicarboxylic acid of formula (I) can be included in cosmetic formulations, whether in the form of emulsions or anydrous compositions, while providing sunscreen protection to the area of the body coated with the cosmetic formulation and, in addition, can be included in a cosmetic formulation to increase the refractive index of the oil phase to more closely equal the refractive index of the water phase such that when the two phases are mixed and emulsified, the formulation will be clear or transparent.

SUMMARY OF THE INVENTION

In brief, the invention is directed to dibenzoylmethane derivative-stabilizing and/or skin protecting and/or gloss-imparting and/or hair color protecting compounds comprising a diester of a naphthalene dicarboxylic acid, while providing UV absorption.

The active dibenzoylmethane derivative-stabilizing and/or skin protecting and/or gloss-imparting and/or hair color protecting compounds of the invention are diesters of a naphthalene dicarboxylic acid.

A diester of the invention has the structure (I):

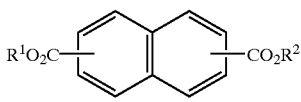

(I)

wherein $R^1$ has the formula (II),

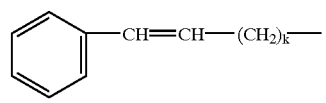

(II)

wherein k is 1 to 13, preferably 1 to 6, most preferably 1, and $R^2$, same or different, is selected from the group consisting of a compound of formula (II) wherein k is 1 to 13, preferably 1 to 6, most preferably 1, and an alkyl group, straight chain or branched, having 1 to 22 carbon atoms, and mixtures thereof.

The diesters are reaction products of (a) a naphthalene dicarboxylic acid having the structure (III):

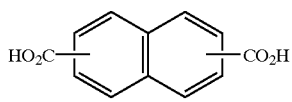

(III)

and an alcohol having the structure $R^2$—OH, wherein $R^2$ is defined as above, or a mixture thereof.

The naphthalene dicarboxylic acid is selected from the group consisting of 1,2-naphthalene dicarboxylic acid; 1,3-naphthalene dicarboxylic acid; 1,4-naphthalene dicarboxylic acid; 1,5-naphthalene dicarboxylic acid; 1,6-naphthalene dicarboxylic acid; 1,7-naphthalene dicarboxylic acid; 1,8-naphthalene dicarboxylic acid; 2,3-naphthalene dicarboxylic acid; 2,6-naphthalene dicarboxylic acid; 2,7-naphthalene dicarboxylic acid, and mixtures thereof. Preferred dicarboxylic acids are the 2,6-, 1,5- and 1,8-naphthalene dicarboxylic acids.

The alcohol $R^2$—OH can be, for example, methanol, ethanol, propanol, isopropyl alcohol, n-butanol, sec-butanol, isobutyl alcohol, tert-butyl alcohol, amyl alcohol, 1-hexanol, 1-octanol, 1-decanol, isodecyl alcohol, 1-undecanol, 1-dodecanol, 1-tridecyl alcohol, 1-tetradecanol, 1-hexadecanol, 1-octadecanol, 1-eicosonol, 1-decosonol, 2-ethylhexyl alcohol, 2-butyloctanol, 2-butyldecanol, 2-hexyldecanol, 2-octyldecanol, 2-hexyldodecanol, 2-octyldodecanol, 2-decyltetradecanol, cinnamyl alcohol (cinnamic alcohol), and mixtures thereof.

Surprisingly, it has been found that compounds having formula (I) are quire effective in photochemically stabilizing dibenzoylmethane derivatives.

Accordingly, one aspect of the invention is to provide a composition for application to human skin and hair that photochemically stabilizes dibenzoylmethane derivatives, particularly PARSOL® 1789, and capable of increasing the sunscreen protection factor (SPF) achievable for sunscreen compositions containing the dibenzoylmethane derivatives.

Another aspect of the invention is to provide an improved, stable composition containing a diester of a naphthalene dicarboxylic acid that increases the effectiveness of dibenzoylmethane derivative sunscreen compounds, particularly 4-(1,1-dimethylethyl)-4'-methoxydibenzoylmethane (PARSOL® 1789), in SPF and in duration, for protection of human skin and hair.

Another aspect of the invention is to provide a stable, broad spectrum sunscreen composition for topical application to human skin and hair that has a SPF of at least 12 and provides substantial protection against the full range of solar UV radiation (280–400 nm), including about 4–15% by weight of a diester of naphthalene dicarboxylic acid, and contains less than 7% and preferably less than 6.1% of sunscreen composition additives selected from the group oxybenzone and avobenzone (PARSOL 1789).

Still another aspect of the invention is to provide a moisturizing composition for topical application to human skin and hair that provides an SPF of at least 20, including about 4–15% by weight of a diester of naphthalene dicarboxylic acid.

These diesters of naphthalene dicarboxylic acids are quite effective in imparting hair gloss and preserving a desired natural or dyed hair color, while providing the hair with sunscreen protection, when contained in a composition in an amount of at least about 0.1% by weight, up to about 20% by weight, preferably about 0.2% to 10% by weight, more preferably about 0.5% to 10% by weight.

Accordingly, another aspect of the invention is to provide a composition that includes a diester of one or more naphthalene dicarboxylic acids as a hair gloss-imparting compound, and as a hair color preserving compound, said naphthalene dicarboxylic acid diester compounds having formula (I).

These diesters of naphthalene dicarboxylic acids are also quite effective in formulating clear or transparent cosmetic formulations, having increased emolliency, and in providing UV sunlight protection to skin.

Thus, another aspect of the invention is directed to cosmetic formulations that include one or more emollients and/or skin conditioners, such as a silicone fluid, wherein the cosmetic compositions are useful as antiperspirants, deodorants, emollients, moisturizers, suntan oils, after-shave compositions, transdermal drug compositions, and the like. In the preferred embodiment, the cosmetic formulations comprise an emulsion of an oil phase and a water phase, wherein the water phase includes an emollient, humectant or other organic compound that increases the refractive index of the water phase, and the oil phase includes a sufficient amount of particular diesters of naphthalene dicarboxylic acids to provide the oil phase and the water phase of the cosmetic formulations with approximately the same refractive index, so that the cosmetic formulations are transparent, or clear, as perceived by human eye. In other embodiments, the clear cosmetic formulations may be anhydrous, or include only an oil phase, with thickening agents such as one or more clays, e.g., hectorite or laponite, so that no emulsifying agents are required, but the composition includes one or more of the particular diesters of a naphthalene dicarboxylic acid for emolliency and clarity.

Preferred diesters of naphthalene dicarboxylic acid of the invention have a high refractive index of at least about 1.5, preferably about 1.53, and are added to the oil phase of a oil and water emulsion to provide emolliency and, optionally, transparency to the emulsion, particularly for cosmetic formulations.

The above and other aspects and advantages of the invention will become more apparent from the following detailed description of the preferred embodiments, taken in conjunction with the drawings.

DETAILED DESCRIPTION OF THE PREFERRED EMBODIMENTS

Figure 1:
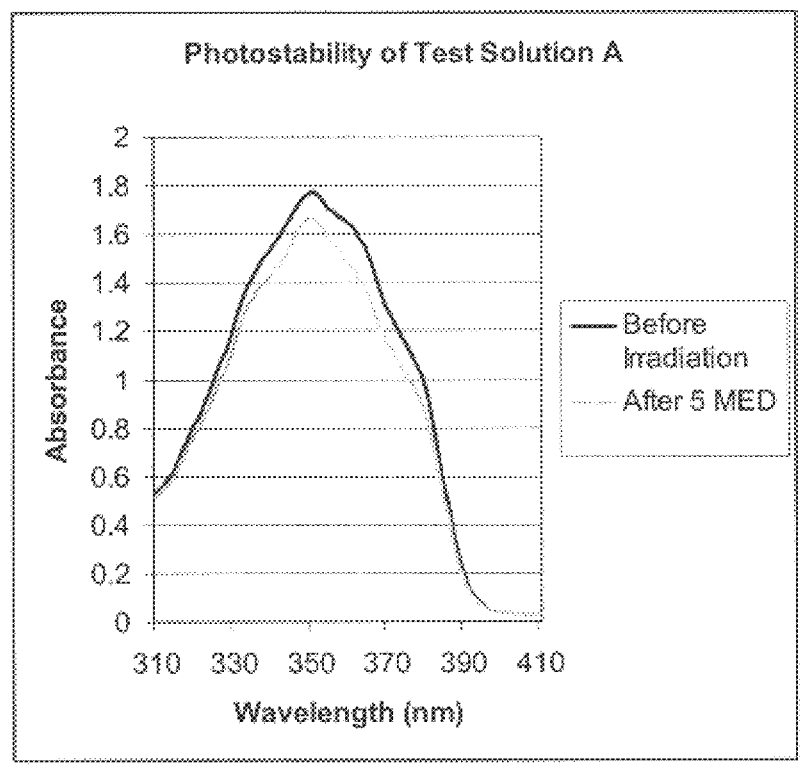
FIG. 1 is a graph showing the photostability (photoinstability) or UV absorbance capability, of a sunscreen composition containing 3% by weight avobenzone when subjected to ultraviolet light of varying wavelengths.

The preferred compositions of the invention include, optionally, about 0.5% to about 5%, preferably about 0.5% to about 3% of a dibenzoylmethane derivative UV-A filter compound, such as 4-(1,1-dimethylethyl)-4'-methoxydibenzoylmethane (PARSOL® 1789) and about 1% to about 10% by weight of a diester of one or more naphthalene dicarboxylic acid photostabilizer/solubilizer for the dibenzoylmethane derivative, having formula (I):

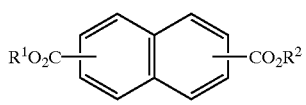

(I)

wherein $R^1$ has the formula (II),

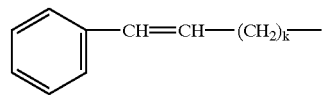

(II)

wherein k is 1 to 13, preferably 1 to 6, most preferably 1, and $R^2$, same or different, is selected from the group consisting of a compound of formula (II) wherein k is 1 to 13, preferably 1 to 6, most preferably 1, and an alkyl group, straight chain or branched, having 1 to 22 carbon atoms, and mixtures thereof.

Typical cosmetic formulations that should be transparent are as follows, having sufficient diester of a naphthalene dicarboxylic acid to provide transparency and/or increased emolliency. In formulations that include emulsified oil and water phases, one or more of a diester of a naphthalene dicarboxylic acid are added to the oil phase in an amount sufficient such that the oil and water phases have an index of refraction within about 0.1, preferably within about 0.05, more preferably within about 0.01. In some cases, it is necessary to add a water-soluble organic or inorganic material, e.g., propylene glycol, to the water phase to raise the refractive index of the water phase to match the refractive index of the oil phase.

EXAMPLES

Example 1

A test compound was prepared by reacting dimethyl 2,6-naphthalate with a blend of 2-ethylhexanol and cinnamyl alcohol in the presence of dibutyltin diacetate catalyst (FASCAT 4200, available from Elf Atochem of Philadelphia, Pa.).

The resulting product was determined by gas chromatography to be approximately 61% diethylhexyl 2,6-naphthalate, 13% methyl/ethylhexyl 2,6-napthalate, and the balance (approximately 25%) a blend of dicinnamyl 2,6-napthalate, methyl/cinnamyl 2,6-naphthalate, and ethylhexyl/cinnamyl 2,6-naphthalate.

Example 2

The following equipment was used to study the photostabilizing properties of the compound of Example 1.

a. Instrument—UV1000S UV Transmittance Analyzer (Labsphere Inc.)

b. Solar Simulator—Model 16S Solar Simulator equipped with a WG 320 filter (transmits UV>290 nm), ouput monitored by a PMA 2105 UV-B DCS Detector (biologically weighted) and controlled by a PMA 2100 Automatic Dose Controller (Solar Light Co.)

c. Software—UV1000S Version 1.27 (Labsphere Inc.)

d. Pipettor-Finnpipette Digital 0.5–10 µl

The dibenzoylmethane derivative used for testing, butylmethoxydibenzoylmethane (Avobenzone, PARSOL 1789, Roche), has a peak absorbance of 350 nm to 360 nm. To determine the relative efficacy of the compound of Example 1 in photostabilizing the dibenzoylmethane derivative, two test solutions, (A) and (B), were prepared as described in Table 1.

TABLE 1

| Ingredient | A | B (Negative Control) |
| --- | --- | --- |
| Butylmethoxydibenzoylmethane | 0.3 g | 0.3 g |
| Compound of Example 1 | 1.0 g | 0.0 g |
| Dioctyl sebacate | 8.7 g | 9.7 g |

Dioctyl sebacate is a good solvent for butylmethoxydibenzoylmethane and is, under the conditions of this experiment, photochemically inert in the presence of butylmethoxydibenzoylmethane. The solutions were stirred until the butylmethoxydibenzoylmethane was completely dissolved.

Slides for testing each solution were prepared as follows. A 10 µl drop of the test solution was applied to the center of a quartz slide (25 mm by 50 mm). A second quartz slide was placed on top and pressure exerted until the liquid spread to completely cover the area of the slide.

Each slide was then subjected to the testing by following procedure. The slide was centered over the lens on the UV Transmittance Analyzer, and a scan of absorbance from 310 nm to 410 nm was made. The slide was then centered over the aperture of the Solar Simulator and irradiated with 5 MED (1 MED, or Minimum Erythemal Dose, is the UV exposure necessary to cause minimum redness in a typical light-skinned subject. 5 MED is equivalent to 105 mJ/cm²). Immediately following irradiation, the slide was again centered over the lens of the UV Transmittance Analyzer and a second scan of absorbance from 310 nm to 410 nm was made.

Figure 2:
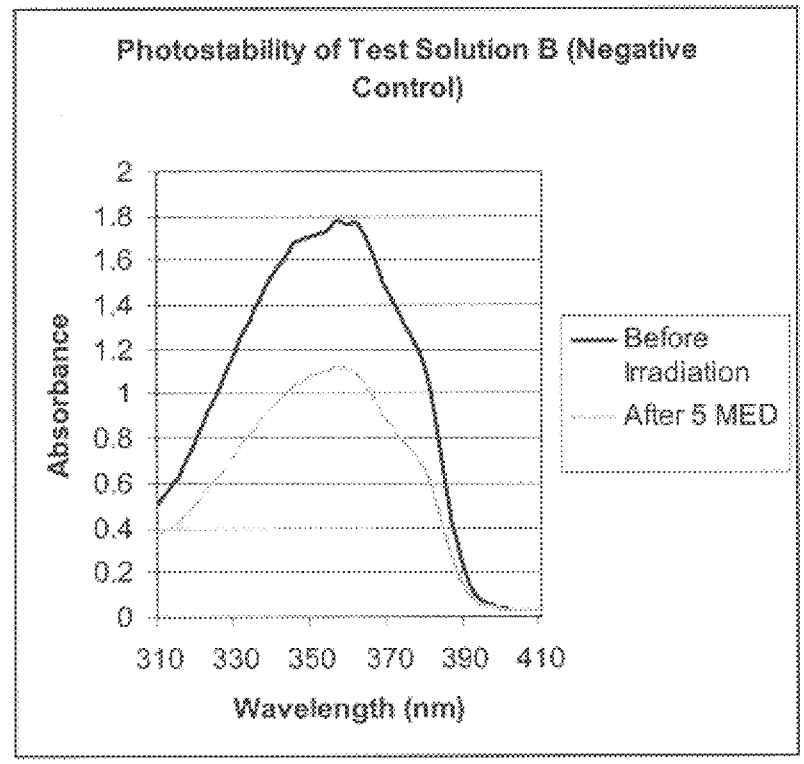
FIG. 2 is a graph showing photostability, or UV absorbance capability, of a sunscreen compositing containing 3% by weight avobenzone when stabilized with 2.5% by weight of a mixture of compounds of formula (I).

The graphs in FIGS. 1 and 2 report absorbance on a logarithmic scale. Absorbance is defined as log(1/T) where T (transmittance) is the ratio of radiation detected after passage through the test vehicle (in this case, through the slide containing the test solution) to radiation emitted by a radiation source. Attenuation is defined as 1-T or, when referred to as a percentage, as 100(1-T). For reference, absorbance of 2.0 equals 99% attenuation, and absorbance of 1.0 equals 90% attenuation.

In each figure, the thicker, darker line represents absorbance before irradiation, and the thinner, lighter line represents absorbance after 5 MED irradiation.

As the figures clearly show, solution A, which contained the compound of Example 1 (see FIG. 1) is much more photostable compared to solution B, the negative control (see FIG. 2). Table 2 directly compares peak absorbance of the two solutions before and after irradiation.

TABLE 2

| Solution | Peak Absorbance Before Irradiation | Peak Absorbance After Irradiation (5 MED) | Percent Loss of Peak Absorbance |
|---|---|---|---|
| A | 1.7772 | 1.6659 | 6.26% |
| B (negative control) | 1.7782 | 1.1185 | 37.10% |

What is claimed is:

1. A diester having the formula (I):

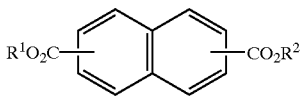

wherein $R^1$ has the formula (II)

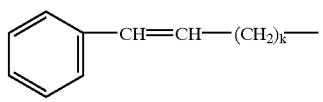

wherein k is 1 to 13; and $R^2$ is selected from the group consisting of formula (II) wherein k is 1 to 13, and an alkyl group, straight chain or branched, having 1 to 22 carbon atoms.

2. A diester of claim 1 wherein k is 1 to 6 in at least one of $R^1$ and $R^2$.

3. A diester of claim 2 wherein k is 1 in at least one of $R^1$ and $R^2$.

4. A diester of claim 1 wherein $R^1$ and $R^2$ are the same.

5. A diester of claim 1 wherein both $R^1$ and $R^2$, same or different, have the formula (II).

6. A diester of claim 5 wherein k is 1 to 6 in at least one of $R^1$ and $R^2$.

7. A diester of claim 6 wherein k is 1 in at least one of $R^1$ and $R^2$.

8. A composition having an SPF of at least 2, for topical application to hair or human skin, in a cosmetically acceptable carrier, comprising at least about 0.1% by weight, based on the total weight of the composition, of a diester of formula (I)

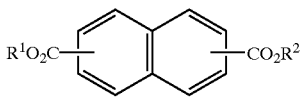

wherein $R^1$ has the formula (II)

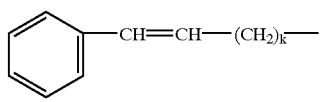

wherein k is 1 to 13, and $R^2$, same or different, is selected from the group consisting of formula (II) wherein k is 1 to 13, and an alkyl group, straight chain or branched, having 1 to 22 carbon atoms.

9. A composition of claim 8 wherein k is 1 to 6 in at least one of $R^1$ and $R^2$.

10. A composition of claim 9 wherein k is 1 in at least one of $R^1$ and $R^2$.

11. A composition of claim 8, further comprising a dibenzoylmethane derivative in an amount of at least 0.5% by weight, based on the total weight of the composition.

12. A composition of claim 11, wherein the molar ratio of said diester to said dibenzoylmethane derivative is about 0.1:1 to about 10:1.

13. A composition of claim 12, wherein the molar ratio of said diester to said dibenzoylmethane derivative is about 0.1:1 to about 0.3:1.

14. A composition of claim 11 wherein said dibenzoylmethane derivative is selected from the group consisting of 4-(1,1-dimethylethyl)-4'-methoxydibenzoylmethane; 4-isopropyl dibenzoylmethane; and mixtures thereof.

15. A composition of claim 14 wherein said dibenzoylmethane derivative is 4-(1,1-dimethylethyl)-4'-methoxydibenzoylmethane.

16. A composition of claim 1 wherein said dibenzoylmethane derivative is included in the composition in an amount of about 0.5% to about 5% by weight, based on the total weight of the composition.

17. A composition of claim 16 wherein said dibenzoylmethane derivative is included in the composition in an amount of about 0.5% to about 3% by weight, based on the total weight of the composition.

18. A composition of claim 11 wherein said diester is included in the composition in an amount of about 0.1% to about 20% by weight, based on the total weight of the composition.

19. A composition, including a carrier selected from the group consisting of water, an organic compound, and mixtures thereof, the improvement comprising about 0.1% to about 20% by weight, based on the total weight of the composition, of a diester of formula (I)

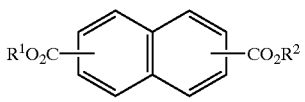

wherein $R^1$ has the formula (II)

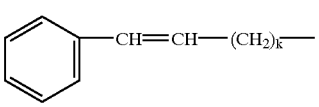

wherein k is 1 to 13; and $R^2$ is selected from the group consisting of formula (II) wherein k is 1 to 13, and an alkyl group, straight chain or branched, having 1 to 22 carbon atoms.

20. A composition of claim 19 wherein k is 1 to 6 in at least one of $R^1$ and $R^2$.

21. A composition of claim 20 wherein k is 1 in at least one of $R^1$ and $R^2$.

22. A composition of claim 19, including an oil phase and a water phase emulsified together to form an oil and water emulsion.

23. A composition of claim 22, further comprising a dibenzoylmethane derivative in an amount of at least 0.5% by weight, based on the total weight of the composition.

24. A composition of claim 23, wherein the molar ratio of said diester to said dibenzoylmethane derivative is about 0.1:1 to about 10:1.

25. A composition of claim 24, wherein the molar ratio of said diester to said dibenzoylmethane derivative is about 0.1:1 to about 0.3:1.

26. A composition of claim 23 wherein said dibenzoylmethane derivative is selected from the group consisting of 4-(1,1-dimethylethyl)-4'-methoxydibenzoylmethane; 4-isopropyl dibenzoylmethane; and mixtures thereof.

27. A composition of claim 26 wherein said dibenzoylmethane derivative is 4-(1,1-dimethylethyl)-4'-methoxydibenzoylmethane.

28. A composition of claim 23 wherein said dibenzoylmethane derivative is included in the composition in an amount of about 0.5% to about 5% by weight, based on the total weight of the composition.

29. A composition of claim 28 wherein said dibenzoylmethane derivative is included in the composition in an amount of about 0.5% to about 3% by weight, based on the total weight of the composition.

30. A composition of claim 22 wherein the cosmetically acceptable carrier comprises a silicone fluid in an amount of about 1% to about 20% by weight, based on the total weight of the composition.

31. A method of filtering out ultraviolet radiation from human skin comprising topically applying to said skin a composition, in a cosmetically acceptable carrier, comprising a diester of formula (I)

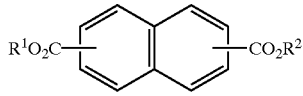

(I)

wherein $R^1$ has the formula (II)

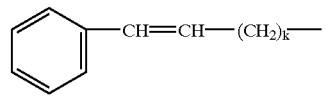

(II)

wherein k is 1 to 13; and $R^2$ is selected from the group consisting of formula (II) wherein k is 1 to 13, and an alkyl group, straight chain or branched, having 1 to 22 carbon atoms.

32. A method of claim 31 wherein k is 1 to 6 in at least one of $R^1$ and $R^2$.

33. A method of claim 32 wherein k is 1 in at least one of $R^1$ and $R^2$.

34. A method of claim 31, wherein said composition further comprises a dibenzoylmethane derivative in an amount of at least 0.5% by weight, based on the total weight of the composition.

35. A method of claim 34 wherein the molar ratio of said diester to said dibenzoylmethane derivative is about 0.1:1 to about 10:1.

36. A method of claim 35, wherein the molar ratio of said diester to said dibenzoylmethane derivative is about 0.1:1 to about 0.3:1.

37. A method of claim 34 wherein said dibenzoylmethane derivative is selected from the group consisting of 4-(1,1-dimethylethyl)-4'-methoxydibenzoylmethane; 4-isopropyl dibenzoylmethane; and mixtures thereof.

38. A method of claim 37 wherein said dibenzoylmethane derivative is 4-(1,1-dimethylethyl)-4'-methoxydibenzoylmethane.

39. A method of claim 38 wherein said dibenzoylmethane derivative is included in the composition in an amount of about 0.5% to about 5% by weight, based on the total weight of the composition.

40. A method of claim 39 wherein said dibenzoylmethane derivative is included in the composition in an amount of about 0.5% to about 3% by weight, based on the total weight of the composition.

41. A method of claim 31 wherein said diester is included in the composition in an amount of about 0.1% to about 20% by weight, based on the total weight of the composition.

42. A method of stabilizing the color of natural or synthetic dye-containing hair comprising the step of topically applying to said hair a composition, in a cosmetically acceptable carrier, comprising 0.1% to 20% by weight, based on the total weight of the composition, of a diester of formula (I)

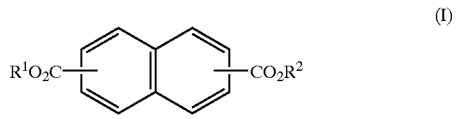

(I)

wherein $R^1$ has the formula (II)

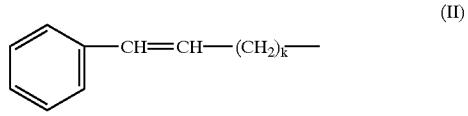

(II)

wherein k is 1 to 13; and $R^2$ is selected from the group consisting of formula (II) wherein k is 1 to 13, and an alkyl group, straight chain or branched, having 1 to 22 carbon atoms.

43. A method of claim 42 wherein k is 1 to 6 in at least one of $R^1$ and $R^2$.

44. A method of claim 43 wherein k is 1 in at least one of $R^1$ and $R^2$.

45. A method of claim 42, wherein said composition further comprises a dibenzoylmethane derivative in an amount of about 0.5% to about 5% by weight, based on the total weight of the composition, and wherein the molar ratio of said diester to said dibenzoylmethane derivative is about 0.1:1 to about 10:1.

46. A method of claim 45, wherein the molar ratio of said diester to said dibenzoylmethane derivative is about 0.1:1 to about 0.3:1.

47. A method of claim 46 wherein said dibenzoylmethane derivative is selected from the group consisting of 4-(1,1-dimethylethyl)-4'-methoxydibenzoylmethane; 4-isopropyl dibenzoylmethane; and mixtures thereof.

48. A method of claim 47 wherein said dibenzoylmethane derivative is 4-(1,1-dimethylethyl)-4'-methoxydibenzoylmethane.

49. A method of claim 48 wherein said dibenzoylmethane derivative is included in the composition in an amount of about 0.5% to about 3% by weight, based on the total weight of the composition.

50. A method of imparting gloss to human hair comprising the step of topically applying to said hair a composition, in a carrier, comprising a diester of formula (I)

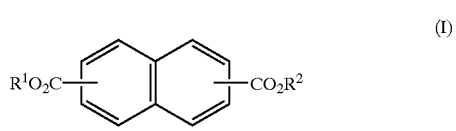

(I)

wherein $R^1$ has for formula (II)

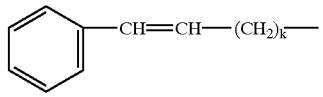
(II)

wherein k is 1 to 13; and $R^2$ is selected from the group consisting of formula (II) wherein k is 1 to 13, and an alkyl group, straight chain or branched, having 1 to 22 carbon atoms.

51. A method of claim 50 wherein k is 1 to 6 in at least one of $R^1$ and $R^2$.

52. A method of claim 51 wherein k is 1 in at least one of $R^1$ and $R^2$.

53. A method of claim 50, wherein said composition further comprises a dibenzoylmethane derivative in an amount of at least about 0.5% by weight, based on the total weight of the composition.

54. A method of claim 53, wherein the molar ratio of said diester to said dibenzoylmethane derivative is about 0.1:1 to about 10:1.

55. A method of claim 53 wherein said diester is included in the composition in an amount of about 0.1% to about 20% by weight, based on the total weight of the composition.

* * * * *